United States Patent [19]

Pury et al.

[11] 4,107,590

[45] Aug. 15, 1978

[54] POWER ASSIST DEVICE USING STRAIN RESPONSIVE MEANS

[75] Inventors: Thomas Pury, Brookfield; Menachem Assa; Howard R. Wagner, both of Milwaukee, all of Wis.

[73] Assignee: General Electric Company, Schenectady, N.Y.

[21] Appl. No.: 733,644

[22] Filed: Oct. 18, 1976

[51] Int. Cl.² .............................................. G05B 11/01
[52] U.S. Cl. ..................................... 318/628; 250/449
[58] Field of Search ...................... 318/628, 646, 488; 250/449, 522, 523, 525

[56] References Cited

U.S. PATENT DOCUMENTS

| 3,693,066 | 9/1972 | Friedman et al. | 318/576 |
|---|---|---|---|
| 3,866,048 | 2/1975 | Gieschen et al. | 250/449 |
| 3,891,856 | 6/1975 | Amor et al. | 250/523 |
| 3,986,090 | 10/1976 | Hecker et al. | 318/488 |
| 4,021,715 | 5/1977 | Von Hacht et al. | 318/628 |

*Primary Examiner*—Robert K. Schaefer
*Assistant Examiner*—John J. Feldhaus
*Attorney, Agent, or Firm*—Ralph G. Hohenfeldt

[57] ABSTRACT

In apparatus wherein a massive component, such as the spot film device of an x-ray table, is driven to various positions with an electric motor drive, a handle is attached to the component for urging it in the desired direction. The handle is attached to the component with beams that flex slightly. A piezoresistive strain gage assembly is mounted on one of the beams for developing an error signal in response to the handle being urged in either direction. The signal is amplified and used to control the power assist driving motor. Means are provided for compensating the vertical component of gravitational force when the handle and the object to which it is attached are angulated. Means are also provided for disabling the drive motor if an electronic element fails.

15 Claims, 6 Drawing Figures

POWER ASSIST DEVICE USING STRAIN RESPONSIVE MEANS

BACKGROUND OF THE INVENTION

This invention relates to a power assist device for use in apparatus where it is desired to cause a motor to position a heavy object in response to a small manual force being applied to an operating handle. Although the device is useful in many kinds of machines, all illustrative example of its construction and use will be described herein in connection with a diagnostic x-ray table.

A typical use of the new power assist device is in an x-ray table which is equipped with a spot-film device. A spot-film device includes a carriage which is mounted in the body of an x-ray table for being moved longitudinally thereof. Supported on the carriage above the table is an enclosure which may be adapted for accommodating a film cassette and an x-ray image intensifier. The enclosure is usually mounted on the carriage in such manner that it may be shifted to various lateral positions relative to the x-ray table top.

It is customary to have a manually engageable handle attached to the enclosure. The operator may then grasp the handle and push or pull the enclosure to position it laterally as required. Heretofore, a handle has also been provided to enable the operator to apply a force in a longitudinal direction for activating an electric motor that drives the heavy carriage to its desired longitudinal position. The carriage is usually affiliated with a counterweight system which assists in balancing the substantial weight of the carriage and spot-film device when the table is angulated.

In some prior art x-ray tables, the operating handle is mounted for pivoting or sliding through a perceptible distance so that when a force is applied, the handle may actuate potentiometers or switches which select motor speed and direction for longitudinal positioning of the spot film device. In some cases switches have been provided which were merely turned a motor control on and off to select direction. In using this prior art system, the operator is deprived of the naturally expected feeling of proportionality between the magnitude of the manually applied force and the rate and direction in which the spot film device moves. In other words, the expected sensation of having moved a mass is not fed back to an operator who uses one of the prior art handles.

An objective of prior designs was to have the motor drive at a speed that is proportional to the amount of manual force applied to the operating handle. Despite extensive efforts at refinement, however, it has been found that in proportional systems where potentiometers or switches are used to initiate driving action, the operator does not get a true sense or feeling of the massive component moving in proportion to the force which is being applied. Moreover, most prior art systems deactivate brakes coincident with application of a force on the operating handle and the brakes are reset as soon as the force is removed. In systems with or without brakes, however, there is invariably some under-travel or over-travel which, again, results in the operator experiencing an unnatural response. Some operators have objected to prior power driven or power assisted systems as feeling too spongy or too soft and as failing to have the spot film device come to rest where one would expect it to.

SUMMARY OF THE INVENTION

An object of the present invention is to overcome the above noted disadvantages by providing an interface between an operator and the machine that allows positioning of a large motor driven mass, such as an x-ray fluoroscopic imaging assembly which normally contains a spot film device and an x-ray image intensifier, so that proportionality between the force applied and movement produced makes it feel to the operator as if a much smaller mass is being moved directly.

In general terms, in accordance with the invention, an operating handle is coupled to a motor driven machine component with a flexure beam (hereinafter called a flexure) that will bend or yield imperceptibly when a manual force is applied to the handle. A second beam is mounted to bend or yield correspondingly. At least one beam has piezo-resistive elements bonded on it. Slight bending causes resistance changes in the elements and production of corresponding error signals which are suitably processed for causing an electric motor to drive the machine component in the same direction in which the force is applied to the handle and at a rate that is proportional to the force applied to the handle.

Other objects are to provide an operating handle for controlling a force amplification system to selectively position a machine component where the sensation of the full mass of the component is not reflected to the operator using the handle and where there is no perceptible motion of the handle relative to the component and, hence, no perceptible motion between the operator and the massive component.

Another object of this invention is to cause the drive system to be disabled if failure of a stress sensing electric circuit component should occur.

Still another object of the invention is to compensate the highly sensitive power assist device for the avoidance of any driving movement which might otherwise result when the angulation or attitude of an operating handle is changed substantially from horizontal so as to produce a vertical gravitational force component which might result in part of the weight of the handle causing the beams to bend minutely and the motor to drive.

How the foregoing and other more specific objects of the invention are achieved will appear in the course of the ensuing description of an illustrative embodiment of the invention which will now be set forth in reference to the drawings.

DESCRIPTION OF A PREFERRED EMBODIMENT

Figure 1:
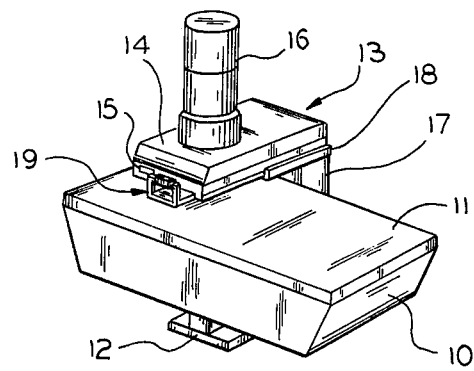
FIG. 1 is a perspective view of a diagnostic x-ray table in which the new power assist device may be used.

In FIG. 1, a typical diagnostic x-ray table in which the new power assist device may be used comprises a housing or body 10 having an x-ray permeable patient supporting top 11. The table is mounted on a stand 12 in a conventional manner such that it is subject to being tilted or angulated longitudinally. The table has x-ray imaging apparatus, generally designated by the reference numeral 13, for making radiographic films and for electronically amplifying an x-ray image so that it can be displayed on a television monitor, not shown. The imaging assembly comprises a housing, commonly called a tunnel 14. The housing 14 has an opening 15 in its front end for admitting and withdrawing a film cassette.

Mounted on top of the housing is an x-ray image intensifier assembly 16. The imaging assembly 13 is carried on a column 17 which is usually made to be vertically extensible and contractible so that the film plane and the image input plane of the intensifier can be established at any desired height. Column 17 is provided with tracks such as 18 on which the assembly 13 is mounted. Thus, assembly 13 may be manually urged laterally, that is, forwardly and rearwardly as viewed in FIG. 1 to thereby locate it over the table top or to get it out of the way as desired. Column 17 is part of a carriage, not visible, which is mounted in table body 10 on suitable tracks so that the assembly 13 may be translated longitudinally of the table top 11. The invention contemplates that the assembly 13 and carriage will be translated longitudinally under the influence of an electric motor drive, not shown. Any of the well known drive systems may be used such as those which employ a motor, sprockets and chains or pulleys and cables. Also not shown, is the conventional system for counterbalancing the carriage and components carried on it so that the carriage will tend to stay in a fixed position when the table is tilted or angulated from horizontal toward a more vertical attitude.

The x-ray imaging assembly 13 may have manually engageable handle assembly 19 fastened to housing 14. The handle may be gripped and used by an operator to push and pull imaging assembly 13 for positioning it laterally relative to the top 11 of the x-ray table. In this illustrative embodiment of the invention, a longitudinal force may also be applied to handle assembly 19 to activate a drive motor for positioning the imaging assembly 13 at desired longitudinal positions relative to the table top 11. Handle 19 may be adapted to bring about lateral positioning of imaging assembly 13 with the use of a power assist device but, for the sake of simplicity in describing the basic concepts of the invention, use of the handle in a power assist system for longitudinal movement will be discussed herein.

Figure 4:
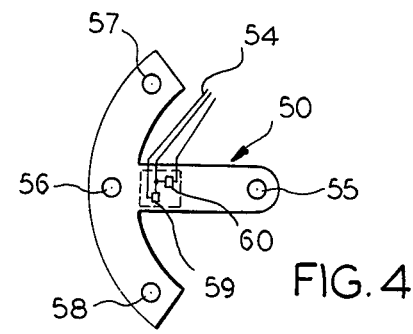
FIG. 4 is an isolated view of a beam on which piezo-resistive elements are mounted.
Figure 5:
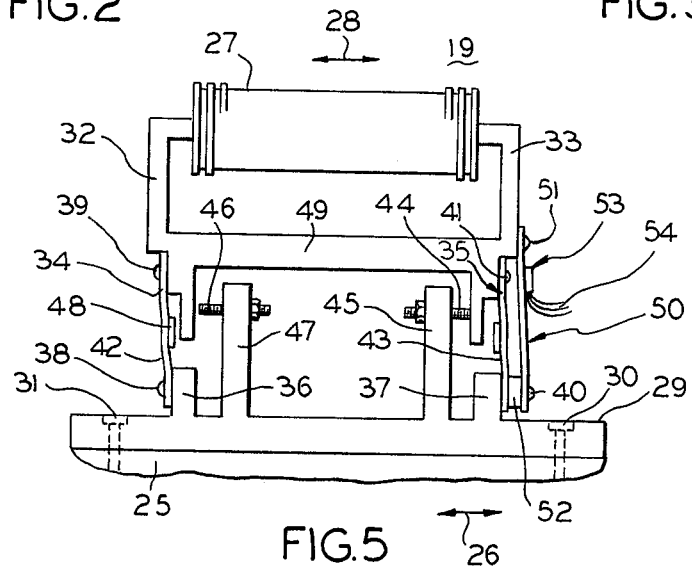
FIG. 5 is a front elevation view, somewhat more diagrammatic than FIGS. 2 and 3, for simplifying explanation of the structure.

A description of one form of handle assembly 19 will now be set forth in reference to FIGS. 2-5. Refer to FIG. 5 wherein a front elevation view of the handle assembly 19 is shown somewhat diagrammatically to facilitate description of its basic features. In this FIGURE, the fragmentarily shown element 25 may be considered part of a machine component which is to be driven bidirectionally, in the directions of the arrow-headed line 26, under the influence of a reversible motor, not shown in this FIGURE. The handle assembly 19 is provided with a manually engageable grip 27 which may be grasped by an operator and urged in either longitudinal direction as suggested by the arrowheads on direction indicating mark 28. As stated earlier, grip 27 may also be grasped when it is desired to move an object such as machine component 25 in a lateral direction, that is, perpendicular to the plane of the drawing in FIG. 5. But, as indicated earlier, for the purpose of illustrating the inventive concepts, only movements in the direction of the arrows 28 will be discussed.

In FIG. 5 the handle comprises a base 29 which may be fastened to the machine component 25 that is to be moved by the drive motor in any manner such as with screws in holes 30 and 31. The handle assembly comprises an element in the shape of a yoke which has two legs 32 and 33 connected by a cross bar 49 that stiffens the legs. Base 29 which is attached to motor driven object 25 is coupled to legs 32 and 33 of the handle by means of relatively thin slightly bendable metal plates or flexures 34 and 35. They may be made of spring bronze and have such thickness and area as to be rigid in respect to forces applied to grip 27 in directions other than longitudinal. Base 29 has upstanding posts 36 and 37. The top end of flexure 34 is fastened to leg 32 of the handle with screws such as 39 and the bottom end is fastened to post 36 with screws 38. Flexure 35 is fastened at its lower end to post 37 with screws such as 40 and to leg 33 of the handle with screws such as 41. Flexures 34 and 35 couple the handle with the object that is to be propelled by the motor. Plates 48 stiffen flexures 34 and 35 except in the longitudinal direction.

In FIG. 5, flexures 34 and 35 are illustrated as having their intermediate portions 42 and 43, respectively, deflected to form opposite ends of a parallelogram such as would result if grip 27 were forced to the left manually. In effect, a horizontal line along the axis of grip 27 would constitute the top of the same parallelogram and the plane of the base would constitute its bottom. Deflection of flexures 34 and 35 is limited in one direction by leg 33 of the handle striking an adjustable stop screw 44 which is mounted in a post 45 extending from the base. A similar adjustable stop screw 46 is mounted in post 47 and arrests movement of handle 19 in the other direction. Of course, when no longitudinal force is applied axially of grip 27 along the line 28, flexures 34 and 35 will be undeflected and in perpendicularity to the horizontal. In a commercial embodiment, the amount of travel by the handle legs 32 and 33 before they hit stops 44 or 46 is on the order of 0.015 inch by way of example and not limitation. Small travel assures that the metal or flexures beams will not fatigue prematurely.

Adjacent flexure 35 in FIG. 5 is a stiffer beam 50 which is fastened at its upper end to leg 33 by means of screws such as 51. The lower end of beam 50 is fastened to post 37 on the base with a screw 40. There is spacer 52 between flexible beam 50 and flexure beam 35 so that the two beams can bend without interferring with each other. Thus, it will be evident that beam 50 will also bend slightly whenever the handle is urged longitudinally. Beam 50 may be made from a plate of aluminium or other metal which will strain significantly with stress and which will restore to its original shape when the main force is relieved from handle 27. In one actual embodiment, the beams have a restoring force of 10 pounds.

As shown diagrammatically in FIG. 5, a strain gage assembly 53 is bonded onto beam 50 and it is subjected to bending stress when beam 50 is bent. Three electric leads 54 extend from the strain gage. The manner in which they are connected will be discussed later in reference to the FIGURE 6 circuit diagram. The strain gage assembly 53 constitutes a transducer for converting a mechanical force into an electric error signal which is used to control the drive motor associated with the machine component that is subject to being moved in response to application of manual force to the handle. Although various transducers 53 might be employed, in a commercial embodiment, a model FL-1-6 beam 50 on which the strain gage elements 53 are mounted was used. The beam and strain gage assembly was obtained from Kulite Semiconductor Products. Inc.

The strain gage beam assembly 50 is shown in FIG. 4 where it is seen to have a T-shaped configuration although it could have other suitable shapes as long as it is adapted for acting as a coupling or connection between a power driven machine component and a handle. Although opposite ends of beam 50 are attached in this example, in some designs the beam might be mounted in cantilever fashion. Screw 40 in FIG. 5 would pass through hole 55 in the beam and screw 51 would pass through hole 56. Further anchoring may be achieved with screws passed through holes 57 and 58. In FIG. 4, two serially connected strain gages 59 and 60 are shown bonded to beam 50 within the confines of a rectangle 61. Three leads 54 extend from the opposite ends and the intermediate point of the serial arrangement. Beam 50 is preferably anchored so that the greatest amount of bending occurs in the region of the strain gages.

Figure 2:
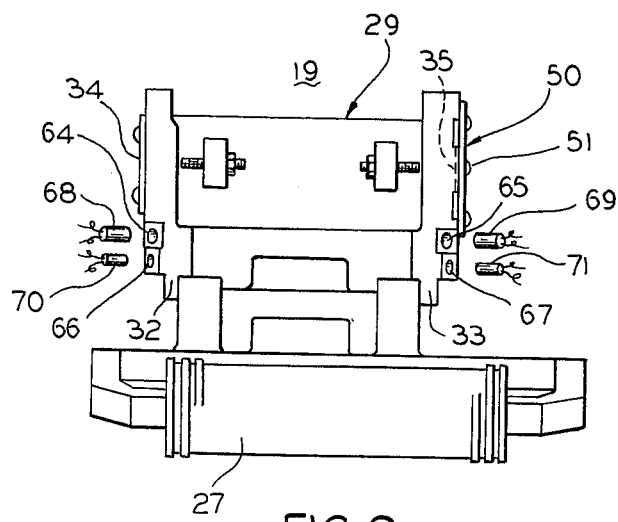
FIG. 2 is a plan view of an illustrative operating handle mechanism comprising a part of the new power assist system.
Figure 3:
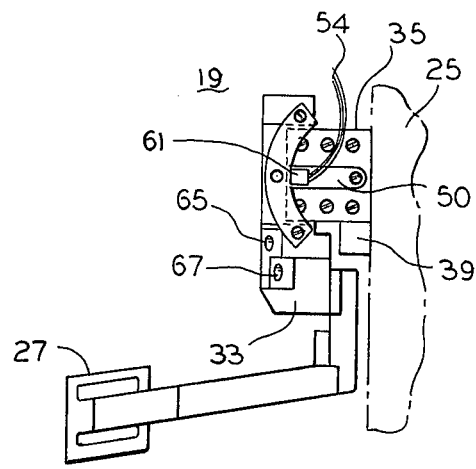
FIG. 3 is an end elevation view of the device in FIG. 2 with some parts removed.

FIGS. 2 and 3 are based on a commercial embodiment of the handle assembly 19 and will be used to explain additional features of it. Parts in this figure corresponding with parts discussed in connection with FIG. 5 have the same reference numerals. Thus, it will be seen that handle assembly 19 comprises a grip 27 and a handle having a pair of legs 32 and 33. The handle is coupled to the base 29 through the agency of slightly bendable spring beams of flexures 34 and 35 and the transducer or strain gage beam 50 is shown attached.

In FIG. 2, one may see that legs 32 and 33 have socket holes 64 and 65 which have their axes, respectively, disposed at the same angle with respect to horizontal and vertical. Adjacent sockets 64 and 65 are another pair of sockets 66 and 67, respectively, which have their axes at the same angle with respect to horizontal and vertical but at a different angle than sockets 65 and 66. Mercury switches 68 and 69 are shown adjacent sockets 64 and 65, respectively, to suggest that these switches are inserted in the sockets. Another pair of mercury switches 70 and 71 are shown adjacent sockets 66 and 67, respectively. When the apparatus such as an x-ray table with which the handle assembly 19 is affiliated is tilted in one direction, mercury switch 66 will close at a first angle such as 19.5°, whose sine is 0.33, from vertical end, when the tilt angle increases to some higher value such as 41.8°, whose sine is 0.66, mercury switch 68 will close sequentially at one-third and two-thirds of 90°. Thus, in this illustrative design, corrections for gravitational influence are made when the apparatus is tilted in the opposite direction, switches 67 and 65 will close in sequence at corresponding angles. The mercury switches, or whatever type of position sensitive switches are used, as will be explained, function to effect compensation for the weight of the handle tending to deflect flexures 34, 35 and beam 50 when the handle is at a substantial tilt angle. Without compensation the servo motor system which is to be described might respond to handle weight as if a small manual force were being applied to the handle in which case the motor might drive the spot-film device slowly but undesirably. Additional mercury switches would be used so that corrections could be made at additional angles in systems that use heavy handles or that are very sensitive to gravity. One switch or no mercury switch could be used in low sensitivity systems.

FIG. 3 shows an end elevation of the handle assembly of FIG. 2 where one may plainly see how one of the flexures 35 couples the handle arm 33 to the object 25 which is to be motor driven. One may also see how the T-shaped beam 50 which carries the transducer assembly 61 also spans between base 39 and handle legs 33. In an actual embodiment, substantially all but the grip portion 27 is surrounded by a cover, not shown, on which the operator may rest his hand without applying any force to the handle and yet keep his hand close to the grip. A hand resting on the grip might cause the highly sensitive system to respond by moving the component.

Figure 6:
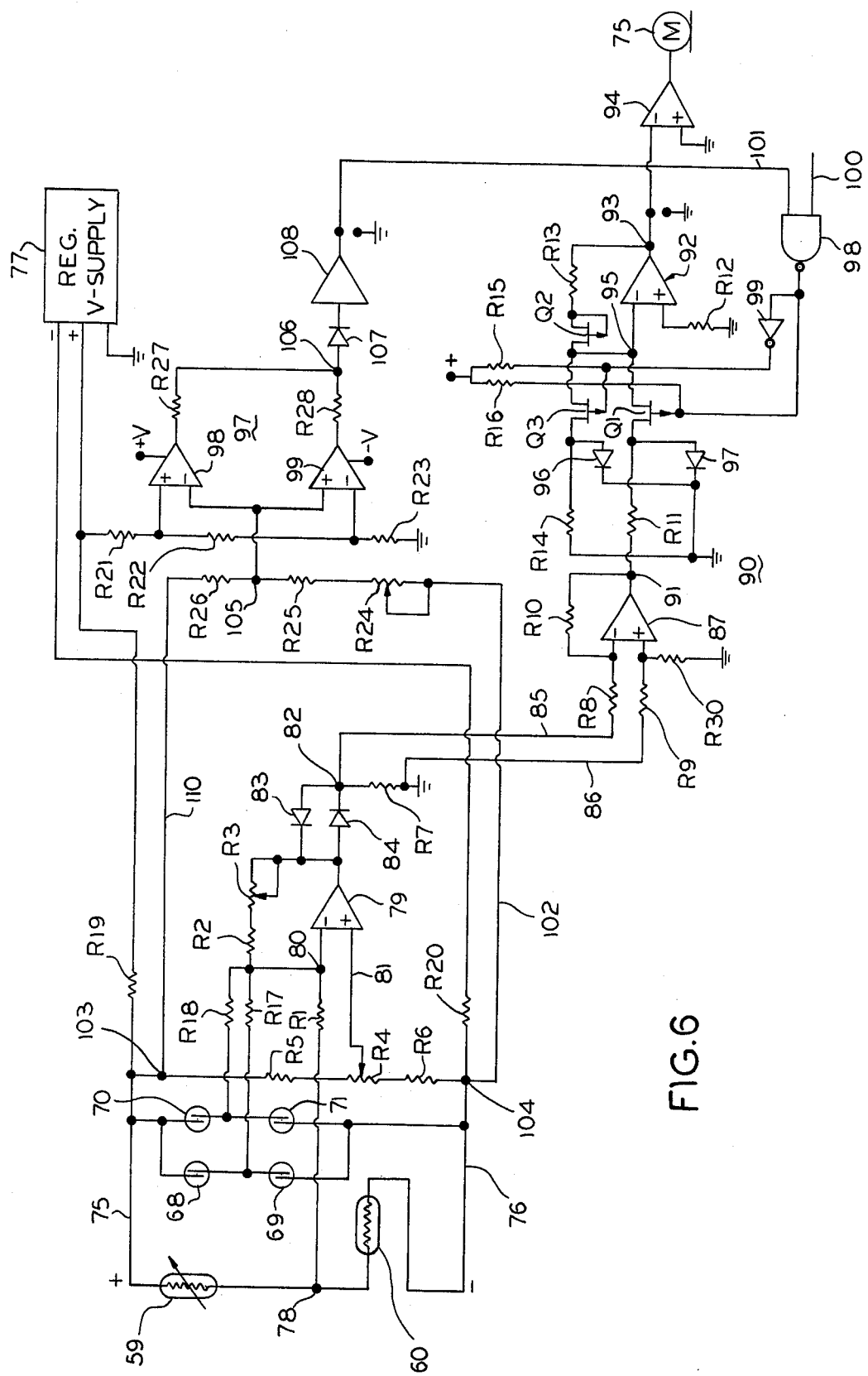
FIG. 6 is an electric circuit diagram for the power assist system.

Refer now to FIG. 6 for a discussion of the electrical features of the power assist system. The motor 75 for driving the carriage which supports the image assembly 13 longitudinally of the x-ray table is shown at the far right of the drawing. The mechanical coupling between the motor and the carriage in the x-ray table is not shown since it is conventional.

At the left of FIG. 6 are shown the piezoresistive elements 59 and 60 which are mounted on flexible beam 50 and which cause the motor to drive the carriage when they are subjected to stress. These elements are in series and have their input means connected between a positive supply line 75 and a negative line 76 which leads back to the output of a stable regulated dual voltage power supply which is shown in block form and marked 77. Current normally flows through the serially connected elements 59 and 60 and an error voltage is produced at the midpoint 78 or this half-bridge when the elements are stressed. Piezoresistive element 59 is mounted on beam 50 in such orientation that its resistance will change when the beam on which it is bonded is bent. Element 60 is arranged at a right angular orientation relative to 59 so its resistance does not change significantly when subjected to bending stress and it serves as a fixed reference. When the operating handle 19 is not subjected to manual stress, a specific voltage signal appears at point 78 intermediate elements 59 and 60 which is the output means of the bridge. When the handle is urged in one direction, an error signal of increasing magnitude and opposite polarity is produced at point 78 and when urged in the opposite direction, a decreased voltage or error signal is developed at point 78. The error signal, after processing, is used to cause motor 75 to be driven in one direction or another at a rate depending on the magnitude and polarity of the error signal at point 78. The error signal is supplied through an input resistor R1 to the inverting input terminal of an operational amplifier 79. A feedback circuit comprised of resistor R2 in series with an adjustable resistor R3 is connected between the output of amplifier 79 and its input or summing point 80. R3 may be adjusted to set the gain of amplifier 79. The noninverting input terminal of operational amplifier 79 is connected by means of a line 81 to a potentiometer resistor R4 which is in a voltage divider circuit comprised of equal value resistors R5 and R6 connected in series between positive line 75 and negative line 76. Potentiometer R4 is adjusted until zero offset of amplifier 79 is obtained, that is, until there is no output from the amplifier when piezoresistive element 59 is not being subjected to bending.

An error signal occurring at point 78 due to bending of the beam 50 by applying a force to the operating handle in one direction or another is amplified by amplifier 79 such that a voltage signal is developed across resistor R7 which is connected between the amplifier output and ground. A pair of oppositely poles diodes 83 and 84 require an output signal from the amplifier which is above their forward threshold voltage. Thus, the diodes provide a small dead band before motor 75 is caused to turn in one direction or another. The voltage signal developed across R7 is supplied over lines 85 and 86 through input resistors R8 and R9 to the inverting and noninverting inputs of a differentially connected operational amplifier 87. This amplifier has the customary feedback resistor R10 connected between its input and output for setting gain.

Operational amplifier 87 is a differential line receiver acting as the input stage to a signal conditioning circuit 90. Error signals from amplifier 87 are delivered from its output terminal 91 through a resistor R11 and a serially connected field effect transistor Q1 to the inverting input of another operational amplifier 92. The output signal having polarity corresponding with the error signal at output terminal 93 of amplifier 92 is supplied to the noninverting input terminal of a servo amplifier 94 which has its noninverting input connected to ground. The output from amplifier 94 causes motor 75 to be driven in one direction or another depending on the polarity of the input error signals developed at point 78 in the first stage of the system. The whole loop 90 comprises a velocity servo so that whole system has good response to input force on the handle and it should be noted that the system response is an anologue of the applied force rather than an on-off response as in prior art systems. Amplifier 92 has a feedback circuit including a resistor R13 in series with a field effect transistor and a jumper 95 which results in the feedback circuit being connected between the output 93 and the noninverting input of amplifier 92. A series circuit including a field effect transistor and a resistor R14 is connected from the feedback circuit to ground. Diodes 96 and 97 are provided to cause the proper bias voltage to be applied to transistors Q1 and Q3. Resistors R11 and R14 preferably have equal values. The gates of transistors Q1 and Q3 are controlled by the condition of the output signal of a NAND gate 98. The output of NAND gate 98 is coupled to the gate of transistor Q3 through an inverter 99. It will be evident that when the output of NAND gate 98 goes high, field effect transistor Q1 will turn off and, due to inverter 99, transistor Q3 will turn on. When the output of NAND gate 98 is low, Q1 will be turned on and Q3 will be off. In other words, when one of Q1 and Q3 is on, the other will be off.

NAND gate 98 has two inputs, 100 and 101. The state of inputs 100 and 101 determines whether the power assist system is to be inactivated or allowed to operate in its normal fashion. It will be evident that when both inputs 100 and 101 to gate 98 are high, the output of the gate will be low in which case Q1 will be on and Q3 will be off. If Q1 is off, the error signal is not applied to the input of amplifier 92 and servo motor amplifier 94 will have no input so the drive motor 75 for the x-ray table carriage cannot drive. On the other hand, if either or both inputs 100 and 101 are low, the output of gate 98 will be high and Q1 will be turned on to enable any error signal which exists to be passed through amplifier 92 and 94, thus causing motor 75 to drive. If no error signal exists, of course, as is the case when no manual force is being applied to operating handle 19, servo amplifier 94 remains nulled and motor 75 does not drive.

Inputs 100 and 101 to NAND gate 98 afford an opportunity to deactivate the motor 75 drive under certain conditions. For instance, a low signal on input 100 might be indicative that electric locks, not shown, are set so as to preclude movement of the carriage in the table in which case the motor 75 should not be allowed to oppose the locks. Thus, a low signal on input 100 would result in a high signal on the outputof gate 98 in which case Q1 would be turned off and the servo amplifier 94 would be held in null.

Input 101 of NAND gate 98 may also handle a signal which when low, will deactivate motor 75 and which when high in conjunction with input 100 being high will allow the motor to run in response to manual handle 19 being urged longitudinally. Both inputs 100 and 101 must be high for motor 75 to be operated. There will be an explanation shortly hereinafter on how the signal applied to input 101 is maintained in a high state during normal operating conditions but is changed to a low state in response to failure of a circuit element so that the power assist system will be deactivated and will not let the carriage drift in the event of such failure.

Incidentally, in signal conditioning circuit 90, the high impedance of field effect transistor Q1 when it is turned off may be sensed as noise by amplifier 92. To assure that no noise pick up occurs, zero volts is applied to both field effect transistors Q1 and Q3 during the turn off state as a result of the presence of R11 and R14. Neither transistor will let the strain gage error voltage through at zero volts. Transistor Q2 in the feedback circuit of amplifier 92 is connected to have very low resistance but is used for compensating the resistance of the other transistors when in their on state. In signal conditioning circuit 90, pull-up resistors R15 and R16 assure that the field effect transistors are properly biased.

As mentioned earlier, the strain gages are so sensitive that the weight of the handle 19 might cause the motor to drift simply due to the weight of the handle deflecting the strain gage and beams when the x-ray table is tilted to a substantial angle from horizontal. Such drift is prevented by use of mercury switches 68–71 which were mentioned earlier. At the input preamplifier state in the left portion of FIG. 6, it will be seen that a pair of mercury switches 68 and 70 are connected to input resistors R17 and R18 of amplifier 79. Both switches 68 and 70 are open when the x-ray table is at an angle between horizontal and a first predetermined tilt angle. When the switches are open the gain of amplifier 79 depends on feedback circuit R2 and R3 and input resistor R1. When the x-ray table is tilted to an angle such that the vertical gravitational vector due to the weight of the handle becomes influential, switch 68 will close and cause a signal to be applied through resistor R17 to the summing point 80 of amplifier 79 such that the output of the amplifier will be reduced. When the table is tilted further to a second predetermined angle, mercury switch 70 will close and cause additional signal to be applied to summing point 80 through resistor R18, thus further reducing the output of amplifier 79 as required. When the table is tilted in the opposite angular direction, the other pair of mercury switches 69 and 71 close sequentially to perform the functions which were performed by switches 68 and 70 as just described. As mentioned earlier, in low sensitivity systems having stiffer flexures, compensation for handle weight may be unnecessary and the mercury switches and their associated resistors need not be employed. In highly sensitive systems, on the other hand, additional switches and summing resistors may be employed to compensate for handle weight at more angular increments.

Another significant feature of the invention is the provision of means for deactivating the drive motor 75 in case of failure of a stress sensing circuit element which might result in an error signal being produced without any force being applied to the operating handle. Turning off the servo drive system in response to failure of a circuit element is achieved by sensing current flow through a resistor R20 in the preamplifier circuit. It will be noted that R20 is in the negative return line to power supply 77. Any change in a predetermined current through R20 is sensed with a window comparator 97. The comparator comprises a pair of operational amplifier 98 and 99 which have resistors R27 and R28, respectively, in series with their outputs. The reference voltage for the comparator is obtained with a voltage divider comprised of resistor R21, R22 and R23. Intermediate points of the divider are connected to the non-inverting input of amplifier 98 and to the inverting input of amplifier 99 as shown. An error signal resulting from failure of a stress sensing circuit component and a change in current through R22 is applied with a divider comprised of any adjustable resistor R24 and resistors R25 and R26. By means of lines 110 and 102, the R24-R26 divider is connected to points 103 and 104, respectively. The voltage at point 104 will have a predetermined range as long as the current through R20 is within a predetermined range. A range is requied since there will be some normal variation in current due to the mercury switches 68-71 cutting in and out. However, if a circuit element short circuits or opens, there will be a substantial change in current through R20 and this will be sensed as a voltage change at the intermediate pooint 105 of the divider. If the voltage change is outside of the window of comparator 97, the comparator will change state and cause the output signal at junction 106 to switch from high to low. This signal is transmitted through a diode 107 to a buffer amplifier 108 whose output will also switch from high to low. This means that the input 101 of NAND gate 98 will go from high to low and the output of the gate will go high. Upon this event, Q1 will turn off as explained earlier and amplifier 92 and servo amplifier 94 for the motor 75 will be deactivated in which case the carriage in the x-ray table will be held in a fixed position. Thus, failure of a stress sensing circuit element cannot result in the motor and carriage running away.

In summary, it will be evident to those skilled in the art that an operating handle such as 19 may be adapted for controlling a motor, not shown, which is used for driving the image assembly housing vertically or laterally or a similar handle may be used to control another, not shown, motor for driving the assembly vertically on extensible column 17. A single handle may be used to control individual components which are motor driven horizontally and vertically, respectively. The handle shown in FIGS. 2 and 3 is designed for easy adaptation to control two motors. As can be seen in FIG. 3, this handle is provided with a laterally extending integral members such as 61 which can be split or made in two parts and these parts may be joined with flexures similar to 34 and 35 which are in parallel with a beam similar 50 on which strain responsive elements such as 59 and 61 are bonded. Then applying a manual force on grip 27 in a direction which would tend to raise or lower the component 25 to which the handle is attached would cause another motor, not shown, to drive the component up or down. The basic concept is to couple a handle to a machine component in such manner that application of a force on the handle in the direction in which it is desired to have the component move will result in a transducer producing a signal that is proportional to the magnitude and direction of the force and then using the signal to control a motor which drives the component.

Although an embodiment of the invention has been described in considerable detail, such description is intended to be illustrative rather than limiting, for the invention may be variously embodied and used and is to be limited only by construction of the claims which follow.

We claim:

1. For use with x-ray apparatus having a moveable component which is subject to being selctively positioned and having motor means operatively coupled to said component for driving it to desired positions; control means comprising:
   manually engageable handle means coupled to said component and subject to having a manual force applied substantially in the direction in which movement of said component is desired,
   strain responsive means having input and output means,
   means for imparting a strain to said strain responsive means in correspondence with the force applied to said handle means,
   said strain responsive means having the property of varying its electric resistance in response to varying the strain imparted thereto,
   voltage source means for providing a voltage to said input means to produce a predetermined output signal at said output means in the absence of a force and to produce an error signal having a magnitude and polarity depending on the magnitude and direction, respectively, of the force applied to said handle,
   non-integrating linear amplifier means having input means for receiving said error signal and having output means, said amplifier means being operative to produce an output signal that is directly proportional in magnitude and polarity to said error signal, and
   means including a servo-amplifier having input means for receiving the amplified error signal and having output means for said component driving motor in a direction and at a rate independent, respectively, on the polarity and magnitude of said error signal.

2. Means as in claim 1 including means to compensate for slight movement of said handle means which may be caused by the force of gravity acting on said handle means when said handle means becomes disposed at an angle comprising:
   means for altering said error signal in response to the angular disposition of said handle means.

3. For use with x-ray apparatus having a moveable component which is subject to being selectively positioned and having motor means operatively coupled to said component for driving it to desired positions; control means comprising:

manually engageable handle means coupled to said component and subject to having a manual force applied substantially in the direction in which movement of said component is desired, strain responsive means having input and output means, means for imparting a strain to said means in correspondence with the force applied to said handle means, said strain responsive means having the property of varying its electric resistance in response to varying the strain imparted thereto, voltage source means for providing a voltage to said input means to produce a predetermined output signal at said output means in the absence of a force and to produce an error signal having a magnitude and polarity depending on the magnitude and direction respectively, of the applied force, and means for operating said motor in response to said error signal, and including means for inactivating said control means in the event of failure of said strain responsive means, comprising:

amplifier means having input and output means, means for producing a signal corresponding with the magnitude of electric current supplied to said strain responsive means and said amplifier means, window comparator means having input means for said signal and having output means which change state in response to said current going above and below a predetermined magnitude indicative of failure, and means coupled with the output means of said comparator means and responsive to one state thereof by enabling said means for operatiang said motor to operate said motor and responsive to another state of said comparator means which corresponds with failure by disabling said means for operating said motor.

4. For use with x-ray apparatus having a moveable component which is subject to being positioned selectively and having motor means operatively coupled to said component for driving it to desired positions; control means comprising:

manually engageable handle means for applying a manual force substantially in the direction in which movement of said component is desired, beam means coupling said handle to said component, said beam means being yieldable by a small amount in response to said force being applied to said handle, strain responsive means mounted to said beam means and subject to having a strain imparted thereto in response to yielding of said beam means, said strain responsive means having the property of varying its electric resistance in correspondence with the strain therein and having input means for being connected to an electric power source and having output means for an error signal that has magnitude and polarity which depends on the amount and direction, respectively, in which said beam means yields, amplifier means having input and output means, the input means of said amplifier means being connected to receive said error signal from said strain responsive means and said amplifier means producing a corresponding output signal, and means for controlling operation of said motor means in response to said last named output signal.

5. Control means as in claim 4 wherein:

said beam means comprises at least two beam elements in spaced relationship and forming the ends of a parallelogram with each other such that said handle will move slightly along a line corresponding with a side of said parallelogram when a manual force is applied thereto.

6. Control means as in claim 4 wherein:

said strain responsive means comprise piezoresistive elements connected in a series circuit with each other, the ends of said circuit comprising said input means for being connected to said electric power source and a point between said elements comprising said output means which is connected to said input means of said amplifier means.

7. Control means as in claim 4 including means to compensate for yielding of said beam means caused by the force of gravity acting on said handle when said handle becomes disposed at an angle said means comprising:

means for altering the input to said amplifier means so as to alter the output thereof, means including switch means operable in response to said handle attaining a predetermined angle to cause said means for altering said input to alter said output of said amplifier means.

8. The means as in claim 7 wherein said amplifier means is an operational amplifier having a summing input terminal, a plurality of input resistor means for said amplifier having first corresponding ends connected to said summing point, a second end of one of said input resistors being connected to said output means of said strain responsive means, said switch means comprising first and second position responsive switches connected in a series circuit with each other and third and fourth position responsive means connected in a series circuit with each other, said voltage source having positive and negative output terminals and said series circuits being connected between said terminals, a second end of another of said input resistor means being connected to a point said first and second switch means and a second end of still another of said input resistor means being connected between said third and fourth switch means whereby when said handle is turned in one angular direction said first and third switch means will close sequentially to apply a signal to said summing terminal to change said output and when said handle is turned in an opposite angular direction said second and fourth switch will close sequentially to apply a signal to said summing˙ terminal to change said output.

9. For use in x-ray apparatus having a moveable component which is subject to being positioned selectively and having motor means for driving said component to desired positions;

manually engageable handle means coupled to said component for applying a manual force in either of opposite directions in which movement of said component is desired, strain responsive means mounted for being strained in response to a manual force being applied to said handle means in either of said directions, said strain responsive means comprising a piezoresistive element, which has the property of varying its electric resistance in response to being strained, and a reference resistive element, a source of d-c voltage, said elements being connected in series with each other and between said source of voltage such that a predetermined signal is developed at a point intermediate said elements when substantially no force is applied to said handle and an error signal is developed at said point when a force is applied to said handle, said error signal having a magnitude and polarity depending on the magnitude and direction of the force applied to said handle, and means including motor control means responsive to said error signal by causing said motor to drive said component during existence of said error signal and in a direction corresponding with the direction in which said manual force is applied.

10. The apparatus as in claim 9 including:

first beam means interposed between said handle means and said component for coupling said handle means thereto, said first beam means being subject to minor deflection under the influence of a manual force being applied to said handle means, second beam means coupled to said handle and subject to being deflected with said first beam means, and elements being secured on said second beam means for being strained by deflection thereof.

11. The apparatus as in claim 10 wherein:

said first beam means comprise a pair of spring metal members which are spaced from each other to form the ends of a parallelogram, a line through said handle disposed in the direction in which manual force is applied constituting a side of said parallelogram.

12. The apparatus as in claim 9 wherein said means responsive to said error signal includes:

first operational amplifier means having an output and inverting and noninverting inputs, input resistor means connected between said inverting input and said point intermediate said elements for supplying said error signal to said inverting input, means for supplying a bias voltage to said noninverting input to compensate the offset of said operational means, impedance means in a feedback circuit which is connected between said operational amplifier output and said inverting input for setting the gain of said amplifier means, and means for coupling said error signal from the output of said first operational amplifier means to said motor control means.

13. The apparatus as in claim 12 having circuit failure detecting means including:

means for producing a signal corresponding with the magnitude of the electric current supplied to said elements and said first amplifier means, window comparator means having input means for said signal and having output means which change state in response to said current going above and below a predetermined magnitude indicative of failure, and means coupled with the output means of said comparator means and responsive to one state thereof by enabling said motor control means to operate said motor and responsive to another state of said comparator means which corresponds with failure by preventing said control means from operating said motor.

14. The apparatus as in claim 12 wherein said handle and component are tiltable through a substantial angle such that the weight of said handle may cause strain to be developed in said strain responsive means, including:

first and second position sensitive switch means connected in a series circuit which is connected across said source of d-c voltage, third and fourth position sensitive switch means connected in a series circuit which is connected across said source of d-c voltage, resistor means having corresponding one ends connected to said inverting input and corresponding opposite ends connected respectively to a point intermediate said first and second switch means and a point between said third and fourth switch means, said first and third switch means being constructed and arranged for closing sequentially when said handle means passes through successive predetermined tilt angles in one direction to thereby change the bias and reduce the sensitivity of said amplifier means, and said second and fourth switch means being constructed and arranged for closing sequentially when said handle means passes through successive predetermined tilt angles opposite to said one direction to thereby change the bias and reduce the sensitivity of said amplifier means.

15. The apparatus as in claim 14 wherein said position sensitive switches are mercury switches.

* * * * *